US012640046B2

(12) United States Patent
Aidan

(10) Patent No.: US 12,640,046 B2
(45) Date of Patent: May 26, 2026

(54) AUGMENTED REALITY ASSISTED HAPTIC FEEDBACK IN MAKEUP APPLICATION

(71) Applicant: ELC MANAGEMENT LLC, Melville, NY (US)

(72) Inventor: Christopher Aidan, Austin, TX (US)

(73) Assignee: ELC MANAGEMENT LLC, Melville, NY (US)

( * ) Notice: Subject to any disclaimer, the term of this patent is extended or adjusted under 35 U.S.C. 154(b) by 0 days.

(21) Appl. No.: 18/779,833

(22) Filed: Jul. 22, 2024

(65) Prior Publication Data

US 2026/0024445 A1     Jan. 22, 2026

(51) Int. Cl.
| | |
|---|---|
| *G09B 5/02* | (2006.01) |
| *A45D 40/00* | (2006.01) |
| *A61B 5/00* | (2006.01) |

(52) U.S. Cl.
CPC .............. *G09B 5/02* (2013.01); *A45D 40/00* (2013.01); *A61B 5/445* (2013.01); *A61B 5/7455* (2013.01); *A45D 2040/0006* (2013.01)

(58) Field of Classification Search
CPC .. G09B 5/02; A45D 40/00; A45D 2040/0006; A61B 5/445; A61B 5/7455
See application file for complete search history.

(56) References Cited

U.S. PATENT DOCUMENTS

| | | | | |
|---|---|---|---|---|
| 10,251,463 | B2 * | 4/2019 | Yamanashi | .......... A45D 44/005 |
| 11,069,094 | B1 | 7/2021 | Evangelista et al. | |
| 11,178,956 | B1 | 11/2021 | Prout | |

| | | | | |
|---|---|---|---|---|
| 2003/0013994 | A1 * | 1/2003 | Rubinstenn | .......... A61B 5/1034 |
| | | | | 600/587 |
| 2013/0309637 | A1 | 11/2013 | Minvielle | |
| 2014/0281950 | A1 * | 9/2014 | White | ..................... G06F 3/016 |
| | | | | 715/269 |
| 2014/0320462 | A1 * | 10/2014 | Tseng | .................. G06F 3/03545 |
| | | | | 345/179 |
| 2015/0050624 | A1 | 2/2015 | Yamanashi et al. | |
| 2015/0254501 | A1 | 9/2015 | Yamanashi et al. | |
| 2017/0046976 | A1 * | 2/2017 | Becker | ................. G09B 19/003 |

(Continued)

FOREIGN PATENT DOCUMENTS

| | | |
|---|---|---|
| WO | WO-2024148963 A1 | 7/2024 |

OTHER PUBLICATIONS

Loreal, "HAPTA Lancome Innovation" Retrieved from the Internet at:https://www.loreal.com/en/articles/science-and-technology/hapta-lancome-innovation/.

(Continued)

*Primary Examiner* — Eddy Saint-Vil
(74) *Attorney, Agent, or Firm* — MARSHALL, GERSTEIN & BORUN LLP

(57) ABSTRACT

The present disclosure provides a handheld makeup applicator device that may analyze the real-time data associated with the face of a user in order to generate a three-dimensional map associated with the face of the user and identify one or more facial features of the face of the user on the three-dimensional map associated with the face of the user. The handheld makeup applicator device may control one or more haptic feedback components to provide haptic feedback as the user holds the handheld makeup applicator device to the face of the user, based on a location of the handheld makeup applicator device with respect to the one or more facial features of the face of the user.

19 Claims, 5 Drawing Sheets

(56)  References Cited

U.S. PATENT DOCUMENTS

| | | | | |
|---|---|---|---|---|
| 2019/0208887 | A1* | 7/2019 | Besen | ...................... G06F 3/012 |
| 2019/0208892 | A1* | 7/2019 | Besen | ................. G06F 3/03545 |
| 2019/0208893 | A1* | 7/2019 | Besen | ...................... G06T 11/60 |
| 2019/0213908 | A1* | 7/2019 | Besen | ...................... G09B 5/02 |
| 2019/0340671 | A1 | 11/2019 | Tran et al. | |
| 2021/0120947 | A1* | 4/2021 | Machiorlette | .......... G09B 19/24 |
| 2021/0307492 | A1 | 10/2021 | Song | |
| 2022/0067380 | A1 | 3/2022 | Hsiao | |
| 2022/0292773 | A1 | 9/2022 | Liu et al. | |
| 2022/0351414 | A1 | 11/2022 | Kosecoff | |
| 2023/0101374 | A1 | 3/2023 | Kosecoff | |
| 2023/0108804 | A1 | 4/2023 | Barron et al. | |
| 2023/0287601 | A1* | 9/2023 | Sugawara | .............. A45D 40/00 |
| 2023/0301417 | A1 | 9/2023 | Lopez | |
| 2024/0065419 | A1 | 2/2024 | Soskic et al. | |
| 2024/0216159 | A1* | 7/2024 | Barbarino | .............. A45D 40/02 |
| 2025/0322601 | A1 | 10/2025 | Lotti et al. | |

OTHER PUBLICATIONS

Borges et al., "A Virtual Makeup Augmented Reality System," 2019 21st Symposium on Virtual and Augmented Reality (SVR), Rio de Janeiro, Brazil, pp. 34-42, 2019. (Year: 2019).

Rahman et al., "Augmented Rendering of Makeup Features in a Smart Interactive Mirror System for Decision Support in Cosmetic Products Selection," 2010 IEEE/ACM 14th International Symposium on Distributed Simulation and Real Time Applications, Fairfax, VA, pp. 203-206, 2010. (Year: 2010).

* cited by examiner

**Handheld Makeup
Applicator Application**

| Select A Look | ▽ |
|---|---|
| Smoky Eye | △ |
| Cat Eye | |
| Contour | |
| Day Look | |
| Night Look | |
| Party Look | |
| Work Look | |
| Celebrity Look | |
| Custom Look | ▽ |

**Handheld Makeup
Applicator Application**

| Select A Look | ▽ |
|---|---|
| Smoky Eye | △ |
| Cat Eye | |
| Contour | |
| Day Look | |
| Night Look | |
| Party Look | |
| Work Look | |
| Celebrity Look | |
| Custom Look | ▽ |

*300*

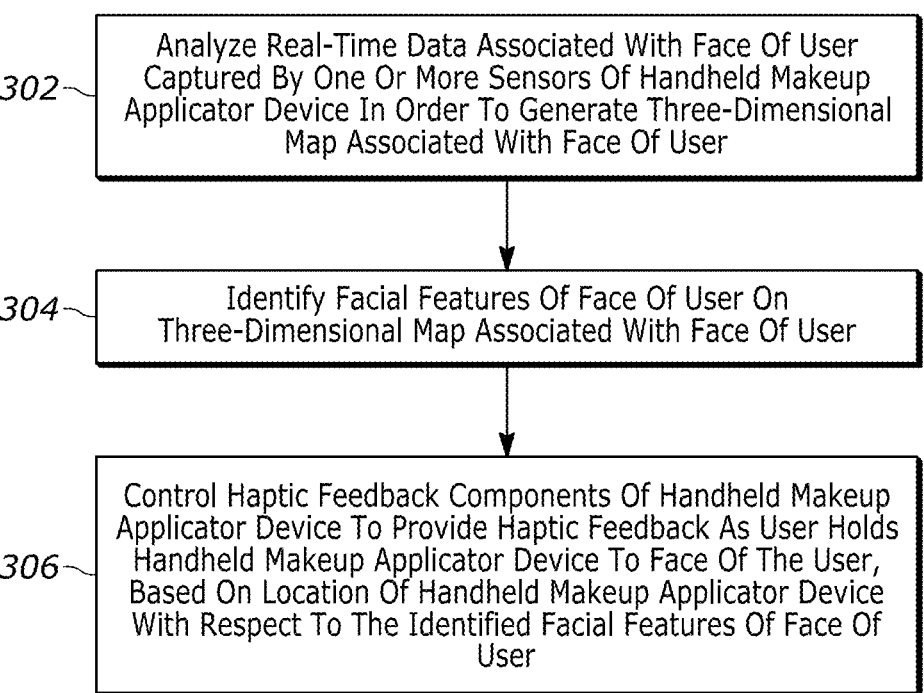

302 — Analyze Real-Time Data Associated With Face Of User Captured By One Or More Sensors Of Handheld Makeup Applicator Device In Order To Generate Three-Dimensional Map Associated With Face Of User 304 — Identify Facial Features Of Face Of User On Three-Dimensional Map Associated With Face Of User 306 — Control Haptic Feedback Components Of Handheld Makeup Applicator Device To Provide Haptic Feedback As User Holds Handheld Makeup Applicator Device To Face Of The User, Based On Location Of Handheld Makeup Applicator Device With Respect To The Identified Facial Features Of Face Of User

FIG. 3

AUGMENTED REALITY ASSISTED HAPTIC FEEDBACK IN MAKEUP APPLICATION

FIELD OF THE INVENTION

The present invention relates generally to the field of cosmetics and, more specifically, to augmented reality-assisted haptic feedback in makeup application, utilizing sensors, haptic components, augmented reality, machine learning, and other technologies.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

The field of cosmetics encompasses a variety of tools and devices aimed at facilitating makeup application. However, traditional makeup applicators typically require manual operation, and manually applying makeup evenly and accurately is a skill-intensive task that poses a particular challenge for individuals with sensory limitations, visual impairments, or motor skill difficulties. For those with such disabilities, the intricate process of makeup application can be daunting, as it often demands fine motor control, a steady hand, and the ability to perceive subtle details.

SUMMARY

In one aspect, a handheld makeup applicator device is provided, comprising: one or more sensors operable to capture real-time data associated with a face of a user; one or more haptic feedback components operable to vibrate to provide haptic feedback to the user; and a controller, comprising: one or more processors; and one or more non-transitory memories storing computer-readable instructions. The computer-readable instructions, when executed by the one or more processors of the controller, may cause the one or more processors to: analyze the real-time data associated with the face of the user in order to generate a three-dimensional map associated with the face of the user; identify one or more facial features of the face of the user on the three-dimensional map associated with the face of the user; and control the one or more haptic feedback components to provide haptic feedback as the user holds the handheld makeup applicator device to the face of the user, based on a location of the handheld makeup applicator device with respect to the one or more facial features of the face of the user. The handheld makeup applicator device may include additional, less, or alternate elements, including those discussed elsewhere herein.

In another aspect, a computer-implemented method for controlling a handheld makeup applicator device via one or more processors is provided. The method may include: analyzing real-time data associated with a face of a user captured by one or more sensors in order to generate a three-dimensional map associated with the face of the user; identifying one or more facial features of the face of the user on the three-dimensional map associated with the face of the user; and controlling one or more haptic feedback components of the handheld makeup applicator device to automatically provide haptic feedback in real-time as the user holds the handheld makeup applicator device to the face of the user, based on a location of the handheld makeup applicator device with respect to the one or more facial features of the face of the user. The method may include additional, less, or alternate actions, including those discussed elsewhere herein.

In still another aspect, a non-transitory computer-readable storage medium storing instructions for controlling a handheld makeup applicator device is provided. The computer-readable instructions, when executed by one or more processors, may cause the one or more processors to perform a method. The method may include analyzing real-time data associated with a face of a user captured by one or more sensors of the handheld makeup applicator device to generate a three-dimensional map associated with the face of the user; identifying one or more facial features of the face of the user on the three-dimensional map associated with the face of the user; and controlling one or more haptic feedback components of the handheld makeup applicator device to automatically provide haptic feedback in real-time as the user holds the handheld makeup applicator device to the face of the user, based on a location of the handheld makeup applicator device with respect to the one or more facial features of the face of the user. The instructions may direct additional, less, or alternative functionality, including that discussed elsewhere herein.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof.

There are shown in the drawings arrangements which are presently discussed, it being understood, however, that the present embodiments are not limited to the precise arrangements and instrumentalities shown, wherein:

FIG. 3 depicts a flow diagram of an exemplary computer-implemented method for controlling a handheld makeup applicator device, according to some embodiments.

Figure 1A:
FIG. 1A depicts an example of a user applying makeup using a handheld makeup applicator device, according to some embodiments.

While the systems and methods disclosed herein are susceptible of being embodied in many different forms, they are shown in the drawings and are described herein in detail specific exemplary embodiments thereof, with the understanding that the present disclosure is to be considered as an exemplification of the principles of the systems and methods disclosed herein and is not intended to limit the systems and methods disclosed herein to the specific embodiments illustrated. In this respect, before explaining at least one embodiment consistent with the present systems and methods disclosed herein in detail, it is to be understood that the systems and methods disclosed herein are not limited in its application to the details of construction and to the arrangements of components set forth above and below, illustrated in the drawings, or as described in the examples.

Methods and apparatuses consistent with the systems and methods disclosed herein are capable of other embodiments and of being practiced and carried out in various ways. Also, it is to be understood that the phraseology and terminology employed herein, as well as the abstract included below, are for the purposes of description and should not be regarded as limiting.

DETAILED DESCRIPTION

Overview

The present disclosure describes a handheld makeup applicator device that may be designed to assist individuals with visual impairments and motor skill challenges in applying makeup with greater accuracy and ease. In some examples, the handheld makeup applicator device may incorporate augmented reality (AR), artificial intelligence (AI), and haptic feedback technology to provide real-time guidance and tactile feedback during the makeup application process.

In some embodiments, the handheld makeup applicator device may include one or more sensors that may capture real-time data associated with the user's face. These sensors may include, for example, a camera or a depth sensor. The handheld makeup applicator device may analyze the real-time data captured by the sensors to generate a three-dimensional map of the user's face and identify facial features on the three-dimensional map of the user' face.

The handheld makeup applicator device may include one or more haptic feedback components that may vibrate to provide tactile feedback to the user. The intensity and pattern of the haptic feedback may be modified based on the proximity of the handheld makeup applicator device to a particular facial feature, such as the eyes, mouth, cheekbones, eyebrows, etc., in some examples, as the user holds the handheld makeup applicator device to their face, to guide the user in applying makeup to the identified facial features, in some examples. In some examples, the haptic feedback may generally guide the user toward the appropriate facial area based on the type of handheld makeup applicator device (e.g., lips for a lipstick applicator, eyelids for an eyeshadow applicator, eyelashes for a mascara applicator, cheeks for a blush applicator, etc.). Furthermore, in some examples, the haptic feedback may assist the user in applying a particular makeup look. For instance, the handheld makeup applicator device may also receive an indication of a makeup look selected by the user from a user interface associated with the handheld makeup applicator device.

The handheld makeup applicator device disclosed herein may provide an innovative solution for individuals with visual impairments and motor skill challenges, enabling them to apply makeup accurately and confidently. By leveraging AR, AI, and haptic feedback technology, the handheld makeup applicator device may offer real-time guidance and tactile feedback, enhancing the makeup application experience and promoting inclusivity and self-expression, in some embodiments.

Example System

FIG. 1A depicts an example of a handheld makeup applicator device 102 in accordance with some embodiments provided herein. As demonstrated in FIG. 1A, the handheld makeup applicator device 102 is equipped with one or more integrated haptic components that generate vibrations or other forms of tactile feedback to guide the user in moving the handheld makeup applicator to the appropriate facial area, and/or in the application of a particular makeup product or a particular makeup look. As shown in FIG. 1A, a user is depicted utilizing the handheld makeup applicator device 102 to apply lipstick. While the example handheld makeup applicator device 102 shown in FIG. 1A specifically illustrates the application of lipstick, it is understood that handheld makeup applicator devices 102 as discussed herein could be configured for the application of other cosmetic products, such as mascara, blush, and the like in various examples.

For instance, a handheld makeup applicator device 102 for lipstick application, as shown in FIG. 1A, may be configured to provide vibrational feedback as the applicator approaches the edge of the user's lips, assisting in applying a lip product with precision. For example, another handheld makeup applicator device 102, designed for blush application, may emit a distinct pattern of vibrations to signal proximity to the user's cheekbones. As another example, a handheld makeup applicator device 102 for eyeliner application may offer specialized haptic feedback to guide the user along the lash line. Each of these handheld makeup applicator devices 102 may utilize specific haptic cues to facilitate accurate placement and movement on the respective facial features, providing tactile guidance that may be particularly beneficial for users with sensory limitations.

Example System

Figure 1B:
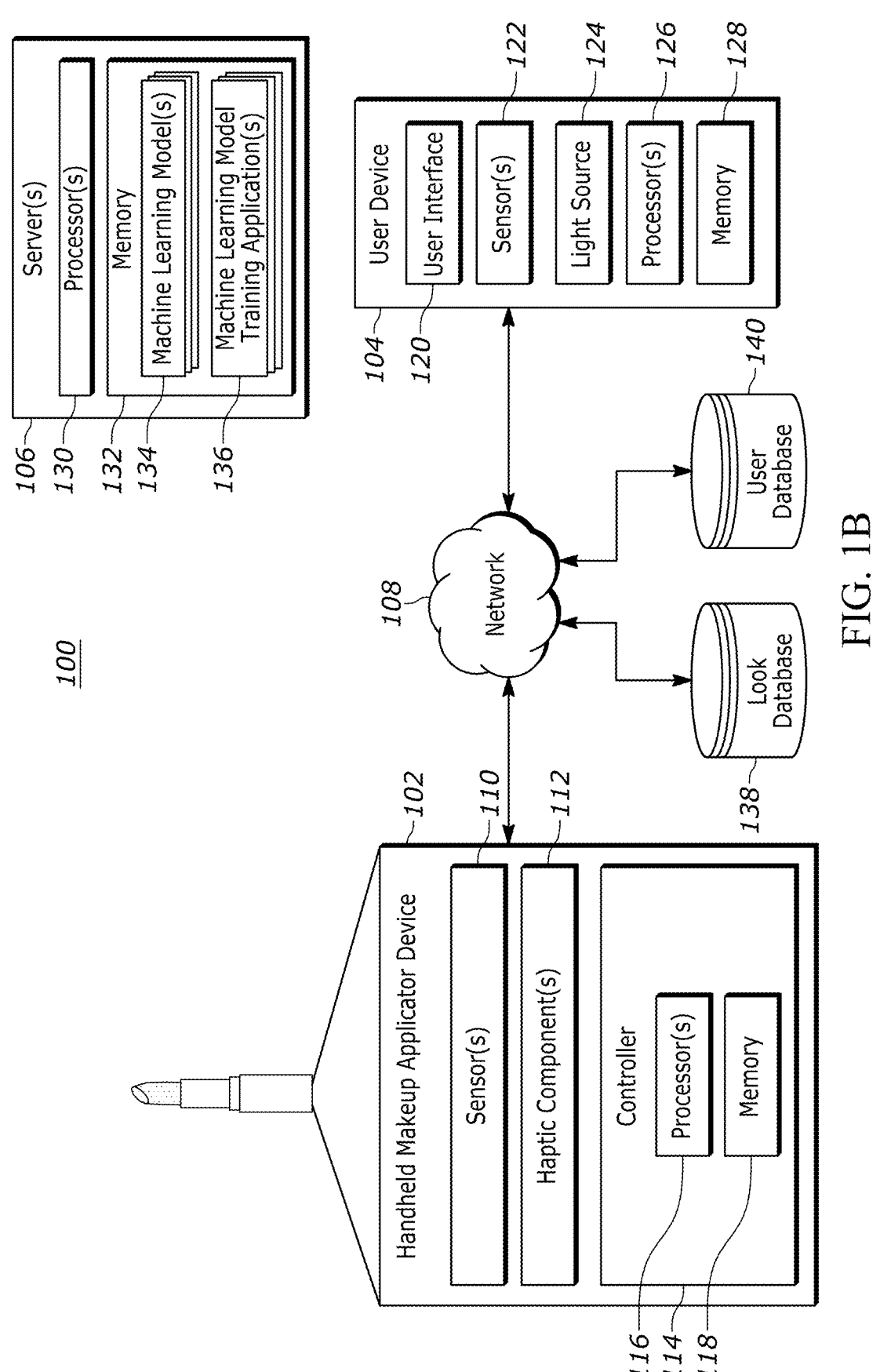
FIG. 1B depicts an exemplary computer system associated with a handheld makeup applicator device, according to some embodiments.

FIG. 1B depicts an exemplary computer system 100 associated with the handheld makeup applicator device 102, according to some embodiments. The high-level architecture illustrated in FIG. 1B may include both hardware and software applications, as well as various data communications channels for communicating data between the various hardware and software components, as is described below.

The exemplary computer system 100 may include a handheld makeup applicator device 102 as well as, in some cases, one or more user devices 104 (which may include, for example, smartphones, smartwatches or fitness tracker devices, tablets, laptops, virtual reality headsets, wearables, etc.), and/or one or more servers 106. The handheld makeup applicator device 102, user devices 104, and/or servers 106 may be operable to communicate with one another via a wired or wireless computer network 108, and/or via short-range signals, such as BLUETOOTH signals.

Although one handheld makeup applicator device 102, one user device 104, one server 106, and one network 108 are shown in FIG. 1B, any number of such handheld makeup applicator devices 102, user devices 104, server(s) 106, and networks 108 may be included in various embodiments. To facilitate such communications, the handheld makeup applicator device 102, user device 104, and/or servers 106 may each respectively comprise a wireless transceiver to receive and transmit wireless communications.

The handheld makeup applicator device 102 may include one or more sensors 110, one or more haptic components 112, and a controller 114.

Generally speaking, the sensors 110 may be operable to capture real-time data associated with the face of a user as a user applies a cosmetic product using the handheld makeup applicator device 102. The sensors 110 may include, for instance, a camera and/or a depth sensor operable to capture data associated with the user's face, distances from various features of the user's face to the handheld makeup applicator device 102, data associated with various cosmetic products to be applied to the user's face and/or their packaging, etc. Moreover, the sensors 110 may include sensors (e.g., the camera and/or the depth sensor, or additional or alternative sensors) operable to capture biometric data associated with the user, such as facial recognition data, fingerprint recognition data, iris recognition data, etc. In some examples, the sensors 110 may include motion or location sensors such as accelerometers, gyroscopes, proximity sensors, etc., in order to detect the location and movement of the handheld makeup applicator device 102 with respect to the user's face.

The haptic component(s) 112 may be configured to vibrate and provide tactile and haptic feedback to the user. The haptic feedback may guide the user moving the handheld makeup applicator device 102 to various facial features of the user, and/or guide the user in applying makeup to the facial features, aiding the user in achieving a desired makeup look. For instance, the haptic feedback provided by the haptic component(s) 112 may be modified based on the proximity of the handheld makeup applicator device 102 to a particular facial feature to assist the user in applying a cosmetic product to the facial feature.

The controller 114 may include one or more processor(s) 116, as well as one or more computer memories 118. The memories 118 of the handheld makeup applicator device 102 may include one or more forms of volatile and/or non-volatile, fixed and/or removable memory, such as read-only memory (ROM), electronic programmable read-only memory (EPROM), random access memory (RAM), erasable electronic programmable read-only memory (EE-PROM), and/or other hard drives, flash memory, MicroSD cards, and others. The memories 118 may store an operating system (OS) (e.g., iOS, Microsoft Windows, Linux, UNIX, etc.) capable of facilitating the functionalities, apps, methods, or other software as discussed herein.

Generally speaking, the memories 118 of the handheld makeup applicator device 102 may store instructions that, when executed by the processor(s) 116, cause the processor(s) 116 to analyze the data associated with the face of the user captured by the sensors 110 in order to generate a three-dimensional map associated with the face of the user and identify one or more facial features of the face of the user on the three-dimensional map associated with the face of the user. Furthermore, the instructions, when executed by the processor(s) 116, may cause the processor(s) 116 to control the haptic components 112 (e.g., via the controller 114) to provide haptic feedback as the user holds the handheld makeup applicator device to his or her face, based on a location of the handheld makeup applicator device with respect to the one or more facial features of the face of the user. For instance, the haptic components 112 may be activated to provide tactile feedback to guide the user to bring the handheld makeup applicator device 102 closer to particular facial features, and/or to guide the user to apply a selected makeup look using the handheld makeup applicator device 102, based on the determined location of the handheld makeup applicator device 102 with respect to the facial features of the user.

That is, the instructions stored on the memories 118 may cause the controller 114 to provide haptic feedback (e.g., via a haptic component 112) in real-time as the user holds the handheld makeup applicator device 102 to the features of the user, to cause the user to hold or move the handheld makeup applicator device 102 in accordance with selected makeup looks. For instance, the instructions stored on the memories 118 may cause the controller 114 to control a haptic component 112 to provide one type of haptic feedback as the user moves the handheld makeup applicator device 102 closer to the targeted feature, and another type of haptic feedback (or no haptic feedback) as the user moves the handheld makeup applicator device 102 further from the targeted facial feature. As another example, the instructions stored on the memories 118 may cause the controller 114 to control a haptic component 112 to provide one type of haptic feedback (or to not provide haptic feedback) when the user's placement or movement of the handheld makeup applicator device 102 is in accordance with the selected makeup looks, and to provide another type of haptic feedback (or to provide haptic feedback) when the handheld makeup applicator device 102 is not in accordance with the selected makeup looks. As another example, the instructions stored on the memories 118 may cause the controller 114 to control a haptic component 112 located on one side or portion of the handheld makeup applicator device 102 to provide haptic feedback to indicate that the user should start (or stop) moving the handheld makeup applicator device 102 in that direction or in that manner, in accordance with selected makeup looks.

For instance, the instructions stored on the memorie(s) 118 may cause the controller 114 to control a haptic feedback component 112 to provide one type of haptic feedback (and/or the absence of haptic feedback) when the handheld makeup applicator device 102 draws a straight line across a user's eyelid for a cat eye look, and another type of haptic feedback (and/or the presence of haptic feedback) when the handheld makeup applicator device 102 begins to draw a crooked line or otherwise veer from an initial straight line based on the way the user is moving or holding the applicator. As another example, the instructions stored on the memorie(s) 118 may cause the controller 114 to control a haptic feedback component 112 to provide a first type of haptic feedback when the user holds the handheld makeup applicator device 102 too close to the eye to apply mascara, a second type of haptic feedback (or the same type of haptic feedback as the first type of haptic feedback) when the handheld makeup applicator device 102 is held too far from the eye to apply mascara, and a third type of haptic feedback (or the absence of haptic feedback) when the handheld makeup applicator device 102 is held the correct distance from the eye to apply mascara. As still another example, the instructions stored on the memorie(s) 118 may cause the controller 114 to control a haptic feedback component 112 to provide one type of haptic feedback when the handheld makeup applicator device 102 is pressed too hard on the lips to apply lipstick in accordance with the selected look, and another type of haptic feedback (or the absence of haptic feedback) when the applicator is pressed to the lips with the correct level of pressure to apply lipstick in accordance with the selected look.

Moreover, the instructions stored on the memories 118 may cause the controller 114 to adapt the haptic feedback provided by the haptic component(s) 112, based on skin conditions detected in real-time, such as blemishes, cuts, or injuries, as captured by the sensor(s) 110 of the handheld makeup applicator device 102 and/or the sensor(s) 122 of the user device 104. For instance, the instructions stored on the memories 118 may cause the processors 116 to analyze image data to identify areas of concern, and may instruct the controller 114 to modify the haptic feedback provided by the haptic component(s) 112 of the handheld makeup applicator device 102 accordingly. This modification may guide the user to apply makeup with greater precision, for instance, by avoiding sensitive areas or by applying additional product to conceal blemishes.

Furthermore, in some examples, the instructions stored on the memories 118 may cause the processors 116 to analyze image data captured by the sensors 110 of the handheld makeup applicator device 102 or sensors 122 of the user device 104 to detect skin conditions of the user, and may, in some cases, cause the controller 114 to adjust or cease the guidance of the handheld makeup applicator device 102 or components thereof to avoid exacerbating any detected skin conditions. Furthermore, in some examples, the instructions stored on the memories 118 may cause the processors 116 to generate an alert based on the detected skin conditions, and provide the alert, e.g., via a user interface component of the handheld makeup applicator device 102 and/or via the user interface of the user device 104.

Moreover, the memories 118 of the handheld makeup applicator device 102 may store instructions that, when executed by the processors 116, cause the processors 116 to analyze images associated with cosmetic products to identify particular cosmetic products or characteristics thereof. For instance, the memories 118 may store instructions that, when executed by the processors 116, cause the processors 116 to capture image data (e.g., via the sensors 110) associated with packaging of various cosmetic products, and analyze the image data associated with the packaging of the various cosmetic products to identify respective cosmetic products based on their packaging.

For instance, in some examples, this analysis may include using object recognition techniques to identify a likely type of cosmetic product and/or likely properties associated with the cosmetic product based on the image. Moreover, in some examples, this analysis may include analyzing an image of the cosmetic product packaging using optical character recognition techniques to identify one or more letters, numbers, words, codes, etc., on the cosmetic product packaging, and accessing a database associated with cosmetic products to match any identified letters, numbers, words, codes, etc., on the cosmetic product packaging with particular cosmetic products and/or particular properties associated therewith. As another example, this analysis may include analyzing an image of the cosmetic product packaging to identify and/or decode a barcode, QR code, etc. For instance, the payload of the barcode, QR code, etc., may include an identification or indication of the cosmetic product and/or properties associated therewith.

Moreover, in some examples, the instructions stored on the memories 118 may cause the processors 116 and/or the controller 114 to perform any or all of the steps of the method 300 discussed below with respect to FIG. 3.

The user computing device 104 may include, or may be operable to communicate with, a user interface 120 of the user computing device 104, which may receive input from users and may provide audible or visible output to users. Furthermore, the user computing device 104 may include, or may be operable to communicate with, one or more respective sensors 122 of the user computing device 104, which may include similar sensors and/or sensor functionality as discussed above with respect to the sensors 110 of the handheld makeup applicator device 102. Additionally, the user computing device 104 may include, or may be operable to communicate with one or more light sources 124 of the user computing device 104.

Moreover, the user computing device 104 may include one or more processors 126, as well as one or more computer memories 128. The memories 128 of the user computing device 104 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memories 128 of the user computing device 104 may store an operating system (OS) (e.g., iOS, Microsoft Windows, Linux, UNIX, etc.) capable of facilitating the functionalities, apps, methods, or other software as discussed herein.

The memories 128 of the user computing device 104 may store instructions that, when executed by the processors 126 of the user computing device 104, cause the processors 126 to receive input from a user as provided via the user interface 120 of the user computing device 104, (e.g., via interactive user interface display screens discussed below with respect to FIGS. 2A-2C), and send the received user input to the handheld makeup applicator device 102 (e.g., via the network 108, in some cases responsive to a request for such user input from the handheld makeup applicator device 102).

Furthermore, in some examples, the memories 128 of the user computing device 104 may store instructions that, when executed by the processors 126 of the user computing device 104, cause the processors 126 to capture sensor data via one or more sensors 122 of the user computing device 104, in some cases responsive to a request for particular sensor data from the handheld makeup applicator device 102 and may send the captured sensor data to the handheld makeup applicator device 102. Moreover, in some examples, the memories 128 of the user computing device 104 may store instructions that, when executed by the processors 126 of the user computing device 104, cause the processors 126 to provide light to the face of the user via one or more light sources 124 of the user computing device 104, in some cases responsive to a request from the handheld makeup applicator device 102 to provide light to the face of the user. In some examples, the request may include a request for particular lighting parameters, such as a particular level/intensity of light, or a particular warmth or color of light, and the processors 126 of the user computing device 104 may in turn cause the light sources 124 of the user computing device 104 to provide the requested level/intensity, color, warmth, etc. of light to the face of the user.

Furthermore, in some examples, the instructions stored on the memories 128 of the user computing device 104 may cause the processors 126 of the user computing device 104 to perform any or all of the steps of the method 300 discussed below with respect to FIG. 3.

In some embodiments, the server(s) 106 may comprise one or more servers, which may include multiple, redundant, or replicated servers as part of a server farm. In further aspects, the server(s) 106 may be implemented as cloud-based servers, such as a cloud-based computing platform. For example, the server(s) 106 may be any one or more cloud-based platform(s) such as MICROSOFT AZURE, AMAZON AWS, or the like. The server(s) 106 may include one or more processors 130 (e.g., CPUs) as well as one or more computer memories 132.

The memories 132 of the server(s) 106 may include various forms of memory such as volatile and non-volatile memory, which can be either fixed or removable. Examples of such memory types include, but are not limited to, read-only memory (ROM), electronic programmable read-only memory (EPROM), random access memory (RAM), and erasable electronic programmable read-only memory (EEPROM). Additional storage options may comprise hard drives, flash memory, and MicroSD cards, among others. These memories 132 are configured to store an operating system (OS), such as Microsoft Windows, Linux, UNIX, or other suitable operating systems, which supports the functionalities, applications, methods, and other software-related aspects described herein.

Additionally, or alternatively, the memories 132 of the server(s) 106 may store makeup look data and/or user data. In some examples, the makeup look data may also be maintained in a look database 138 (or in multiple such databases), accessible or communicatively coupled to the server(s) 106. Similarly, in some examples, the user may reside in a user database 140 (or in multiple such databases), which may be accessible or communicatively coupled to the server(s) 106. Furthermore, in some examples, both makeup look data and user data may be consolidated in a single database, which may be accessible or communicatively coupled to the server(s) 106.

Furthermore, the memories 132 of the server(s) 106 may store instructions that, when executed by the processor(s) 130 of the server(s) 106, cause the processor(s) 130 to receive data from various databases such as look database 138 and user database 140, and/or data from the handheld makeup applicator device 102 and/or the user device 104 (e.g., via the network 108). The data from the handheld makeup applicator device 102 and/or the user device 104 may include, for instance, data captured by the sensor(s) 110 of the handheld makeup applicator device 102 and/or data captured by the sensor(s) 122 of the user device 104, data input by a user via a user interface component of the handheld makeup applicator device 102 (in examples in which the handheld makeup applicator device 102 includes a user interface) and/or data input by a user via the user interface 120 of the user device 104, etc.

The memories 132 of the server(s) 106 may store one or more machine learning model(s) 134, and/or one or more respective machine learning model training application(s) 136. These machine learning model(s) 134 may include, for instance, for instance, a machine learning model trained to analyze data associated with a user's face and/or a three-dimensional map associated with the user's face to identify facial features thereon, a machine learning model trained to analyze images associated with makeup looks to identify cosmetic products and/or techniques used to create the makeup looks, a machine learning model trained to analyze data associated with the user's skin to identify a skin type or a skin health condition associated with the user, a machine learning model trained to analyze data associated with previous makeup looks selected by a user to predict additional makeup looks for the user, etc.

Additionally, the instructions stored on the memories 132 of the server(s) 106, when executed by the processor(s) 130 of the server(s) 106, may cause the processor(s) 130 to analyze data received from the look database 138 and/or the user database 140, and/or the handheld makeup applicator device 102 and/or the user device 104 in order to make an identification or a prediction based on the received data, and subsequently send the identification and/or prediction to the handheld makeup applicator device 102 and/or the user device 104. For instance, this analysis and identification and/or prediction may be based upon applying the trained machine learning model(s) 134 to the data received from the look database 138 and/or the user database 140, and/or the handheld makeup applicator device 102 and/or the user device 104.

In some embodiments, one or more machine learning model(s) 134 may be executed on the server(s) 106, while in other embodiments, one or more machine learning model(s) 134 may be executed on another computing system, separate from the server(s) 106. For instance, the server(s) 106 may transmit data to another computing system, where trained machine learning model(s) 134 are applied to the data, and the other computing system may transmit a prediction or identification, based upon applying the trained machine learning model(s) 134 to the data, back to the server(s) 106. Furthermore, in some embodiments, one or more machine learning model(s) 134 may be trained by respective machine learning model training application(s) 136 executing on the server(s) 106, while in other embodiments, one or more machine learning model(s) 134 may be trained by respective machine learning model training application(s) 136 executing on another computing system, separate from the server(s) 106.

Whether the machine learning model(s) 134 are trained on the server(s) 106 or elsewhere, the machine learning model(s) 134 may be trained by respective machine learning model training application(s) 136 using training data (including historical data in some cases), and the trained machine learning model(s) 134 may then be applied to new/current data that is separate from the training data in order to determine, e.g., predictions and/or identifications related to the new/current data.

For example, machine learning model(s) 134 trained to analyze data associated with facial features of a user and/or a three-dimensional map associated with the facial features to identify facial features thereon may be trained by machine learning model training application(s) 136 using training data including images of various facial features and/or three-dimensional maps associated with the various facial features, and indications of locations of facial features in the images and/or three-dimensional maps. For instance, each image and/or three-dimensional map may be labeled to indicate locations of facial features, and these labeled images and/or three-dimensional maps may be used as training data. Once sufficiently trained using this training data, such machine learning model(s) 134 may be applied to a new image, video, and/or three-dimensional map associated with a user's facial features, and may identify likely locations of various facial features of the particular user.

As another example, machine learning model(s) 134 trained to analyze images associated with makeup looks to identify cosmetic products and/or techniques used to create the makeup looks may be trained by machine learning model training application(s) 136 using training data including images of individuals with various selected looks applied, and indications of cosmetic products and/or techniques that were used to create the selected looks shown in the images. For instance, an image of an individual wearing a particular selected look may be labeled with particular cosmetic products used to create the look, as well as types of devices used to create the selected look, techniques used to create the selected look, etc., and these labeled images may be used as training data. Once sufficiently trained using this training data, such machine learning model(s) 134 may be applied to a new image, such as an image provided by a user via a user interface component of the handheld makeup applicator device 102 and/or a user interface 120 of a user computing device 104, or an image from a social media link provided by the user via a user interface component of the handheld makeup applicator device 102 and/or a user interface 120 of a user computing device 104, and may identify/predict cosmetic products and/or techniques that may be used to replicate the selected looks shown in the image. In some examples, the machine learning model(s) 134 may further generate specifications to be used by the handheld makeup applicator device 102 when replicating the selected looks shown in the image.

Moreover, as another example, machine learning model(s) 134 trained to analyze data associated with the user's skin to identify a skin type or a skin health condition associated with the user may be trained by machine learning model training application(s) 136 using training data including images or other sensor data associated with various individuals' skin, and indications of characteristics associated with the various individuals' skin, as well as any skin conditions of the skin. For instance, images of individuals having various skin types may be labeled with the respective characteristics shown in each image. Similarly, images of individuals having various skin conditions may be labeled with an indication of the skin conditions, the location of visual indicators associated with the skin conditions shown in the image, etc. These labeled images may be used as training data, and once sufficiently trained using this training data, such machine learning model(s) 134 may be applied to a new image, video, and/or three-dimensional map associated with a user's skin (e.g., an image or video captured by the sensor(s) 110 of the handheld makeup applicator device 102, sensor(s) 122 of the user device 104, etc., in real-time), and may identify/predict various characteristics and/or skin conditions associated with the user's skin.

Additionally, as another example, machine learning model(s) 134 trained to analyze data associated with previous makeup looks selected by a user to predict additional makeup looks for the user may be trained by machine learning model training application(s) 136 using training data including makeup looks selected by previous users, characteristics of the previous users, and input/feedback from the previous users about the makeup looks (e.g., provided via the user interface 120), once applied by the handheld makeup applicator device 102. For instance, various makeup looks may be labeled with indications of characteristics of users who gave positive feedback regarding the makeup looks, indications of other makeup looks receiving positive feedback from the same users, etc. Once sufficiently trained using this training data, such machine learning model(s) 134 may be applied to a user, the user's characteristics, and previous makeup looks selected/liked by the user, and may predict/suggest other makeup looks that the user may enjoy.

In various aspects, the machine learning model(s) 134 may comprise machine learning programs or algorithms that may be trained by and/or employ neural networks, which may include deep learning neural networks, or combined learning modules or programs that learn in one or more features or feature datasets in particular area(s) of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques.

In some embodiments, the artificial intelligence and/or machine learning based algorithms used to train the machine learning model(s) 134 may comprise a library or package executed on the server(s) 106 (or other computing devices not shown in the system 100). For example, such libraries may include the TENSORFLOW based library, the PYTORCH library, and/or the SCIKIT-LEARN Python library.

Machine learning may involve identifying and recognizing patterns in existing data (such as training a model based upon historical data) in order to facilitate making predictions or identification for subsequent data (such as using the machine learning model on new/current data order to determine a prediction or identification related to the new/current data).

Machine learning model(s) may be created and trained based upon example data (e.g., "training data") inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based upon the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

The memories 132 of the server(s) 106 may also store additional machine-readable instructions, which may include any of one or more applications, one or more software components, and/or one or more application programming interfaces (APIs). These elements may be implemented to facilitate or perform the features, functions, or other disclosures described herein, such as any methods, processes, elements, or limitations, as illustrated, depicted, or described for the various flowcharts, illustrations, diagrams, figures, and/or other disclosures herein. For instance, in some examples, the computer-readable instructions stored on the memories 132 of the server(s) 106 may include instructions for carrying out any of the steps of the method 300 via an algorithm executing on the processor(s) 130 of the server(s) 106, which is described in greater detail below with respect to FIG. 3. It is to be appreciated that one or more other applications may be envisioned that are executed by the processor(s) 130 of the server(s) 106. Given the advancements in mobile computing devices, any or all of the processes, functions, and steps described herein may be present together on a mobile computing device, such as the user device 104, or the handheld makeup applicator device 102.

Example User Interface Displays

Figures 2A, 2B:
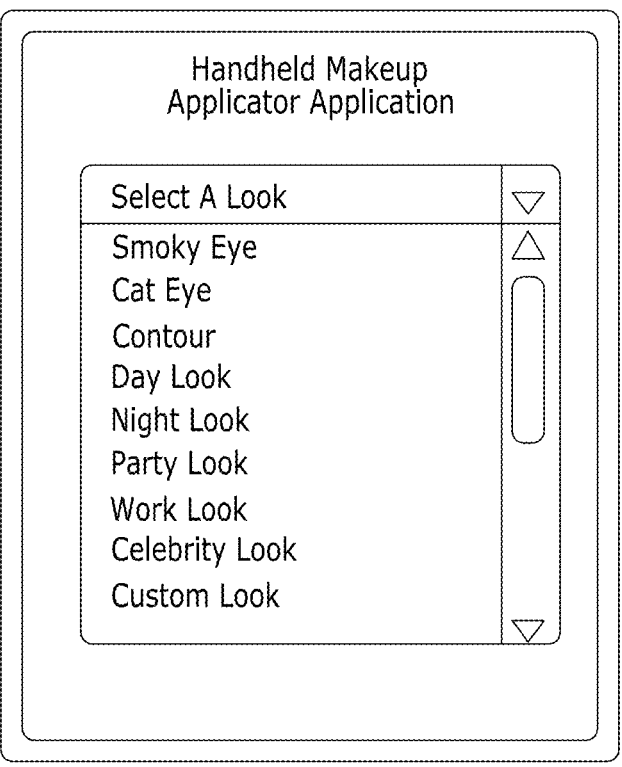
FIGS. 2A-2C depict examples of displays as may be provided by a user interface associated with a handheld makeup applicator device, according to some embodiments.
Figure 2C:
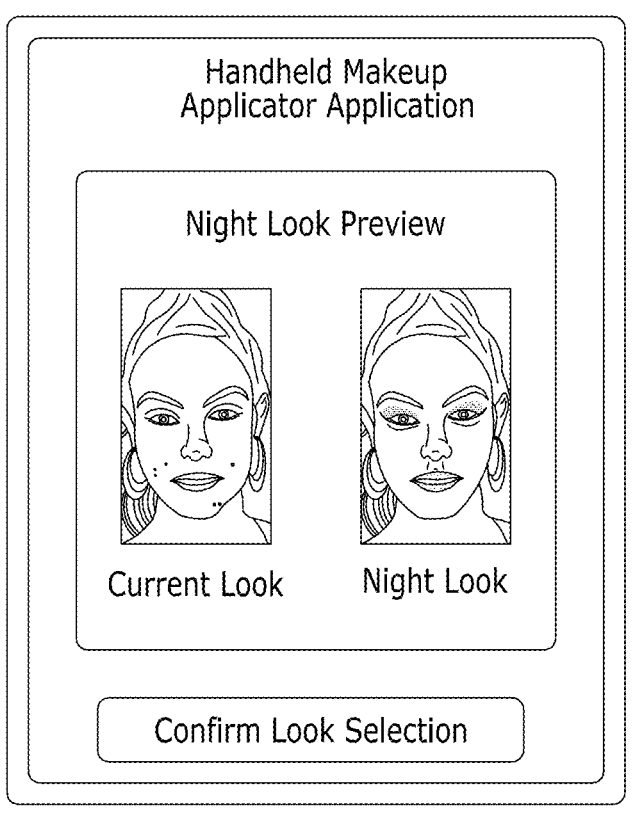

FIGS. 2A-2C depict examples of displays as may be provided by a user interface of the handheld makeup applicator device and/or of an associated user device (e.g., user device 104). For instance, FIG. 2A illustrates an example user interface display via which a user may select a makeup look, and FIG. 2B illustrates an example user interface display via which a user has already selected a makeup look. For instance, the user may select between pre-set options such as "smoky eye," "cat eye," "contour," "day look," "night look," "party look," "work look," "celebrity look," etc. In some examples, the pre-set options may differ based on, for instance, whether a user is subscribed to a makeup look subscription service, or whether the user is operating the handheld makeup applicator device 102 in a "professional" mode compared to an "amateur" mode. Some of these options may include still-further options (not shown)—for instance, a user may select a specific celebrity for a "celebrity look," or may select options for each facial feature to create a custom look. These options may include, for instance, types of products applied, how heavily each of the products are applied to each facial area, etc. Furthermore, in some examples, the user may be prompted to upload an image of a desired look, or a link to a social media post including a desired look, which may be analyzed to generate specifications associated with the desired look for use by the handheld makeup applicator device 102 in generating haptic/tactile feedback to guide a user to apply the selected look.

FIG. 2C illustrates an example preview of the look selected by the user at FIG. 2B. In some examples, the preview may be a generalized preview, e.g., illustrating examples of other individuals to whom the look has been applied, or illustrating examples of a three-dimensional rendering of the look as applied to a three-dimensional model of a face. As shown in FIG. 2C, the preview includes a rendering of the user's current look and a rendering of a predicted look including the selected makeup look. Furthermore, as shown in FIG. 2C, the preview includes an option to confirm the selected look. Upon confirming the selected look, the specifications associated with the selected look may be sent to the handheld makeup applicator device 102, such that the handheld makeup applicator device 102 may generate haptic/tactile feedback to guide a user to apply the selected look.

Example Method

FIG. 3 depicts a flow diagram of an exemplary computer-implemented method 300 for controlling a handheld makeup applicator device 102, according to one embodiment. One or more steps of the method 300 may be implemented as a set of instructions stored on a computer-readable memory, such as memories 118 of the handheld makeup applicator device 102, memories 132 of the server(s) 106, or memories 128 of the user device 104, and executable on one or more processors, such as processor(s) 116 of the handheld makeup applicator device 102, processor(s) 130 of the server(s) 106, or processor(s) 126 of the user device 104.

The method 300 may include analyzing (block 302) real-time data associated with the face of a user captured by one or more sensors in order to generate a three-dimensional map associated with the face of the user. For instance, the sensors may include integrated sensors of the handheld makeup applicator device (e.g., sensors 110, as discussed with respect to FIG. 1B). Additionally, the sensors may include sensors of a separate device, such as a user device (e.g., sensors 122 of the user device 104, as discussed with respect to FIG. 1B), and/or another separate device. The sensors may include, for instance, cameras or depth sensors, or other suitable sensors.

In embodiments in which the sensors include sensors that are part of a separate device, the handheld makeup applicator device may request sensor data from, and/or receive sensor data captured by, the sensors of the separate device via a communication interface of the handheld makeup applicator device, e.g., via a network (e.g., network 108) via a short range signal between the separate device and the handheld makeup applicator device, and/or via a wired connection between the separate device and the handheld makeup applicator device.

Additionally, in some examples, the handheld makeup applicator device, and/or a separate device, may include one or more light sources. In such examples, the method 300 may include controlling light sources integrated into the handheld makeup applicator device to provide light to the face of the user as the sensor data is being captured, or sending a request to the separate device to cause the separate device to activate a light source to provide light to the face of the user as the sensor data is being captured, e.g., via a network (e.g., network 108), via a short range signal between the separate device and the handheld makeup applicator device, and/or via a wired connection between the separate device and the handheld makeup applicator device. For instance, in some examples, the method 300 may include determining optimized lighting parameters, such as an optimized level, warmth, and/or direction of light to be provided based on the selected makeup look, based on a particular cosmetic product being used, based on a particular step within the process of the selected makeup look being applied, and/or based on ambient lighting conditions in an area where the handheld makeup applicator device is being used, and may control an integrated light source to provide the optimized light level, warmth, and/or direction of light, or send a request to the separate device to provide the optimized light level, warmth, and/or direction of light.

In some examples, the method 300 may include generating an augmented reality (AR) version of the three-dimensional map of the face of the user, and displaying the AR version of the three-dimensional map of the face of the user via a user interface associated with the handheld makeup applicator device. As discussed above, in some examples, the user interface may be integrated into the handheld makeup applicator device, and the AR version of the three-dimensional map of the face of the user may be displayed via the user interface of the handheld makeup applicator device. In embodiments in which the user interface is part of a separate device, displaying the AR version of the three-dimensional map of the face of the user may include sending the AR version of the three-dimensional map of the face of the user to the separate device to be displayed by the user interface of the separate device, e.g., via a network (e.g., network 108), via a short range signal between the separate device and the handheld makeup applicator device, and/or via a wired connection between the separate device and the handheld makeup applicator device.

Additionally, the method 300 may include identifying (block 304) one or more facial features of the face of the user on the three-dimensional map associated with the face of the user. In some examples, this analysis may include applying a trained machine learning model to the three-dimensional map associated with the face of the user to identify the facial features. For instance, the method 300 may include training a machine learning model using historical three-dimensional maps associated with other faces, and corresponding portions of the three-dimensional maps associated with facial features of the other faces, and, once trained, the machine learning model may be capable of identifying such facial features on three-dimensional maps associated with new faces. That is, the trained machine learning model may be operable to recognize facial geometry associated with particular facial features on the three-dimensional map associated with a face. Certain facial geometry on a particular location of the face may correspond to the eyes of the face, while other facial geometry at another location of the face may correspond to the lips of the face, etc.

Moreover, in some examples, the method 300 may include generating a preview of the makeup look selected by the user as applied to facial features of the face of the user on the three-dimensional map associated with the face of the user. For instance, the method 300 may include generating an AR preview of the makeup look selected by the user as applied to facial features of the face of the user on the three-dimensional map associated with the face of the user. Furthermore, the method 300 may include generating an AR preview of the steps of the application process of the makeup look selected by the user to the facial features of the face of the user. For instance, the AR preview of the steps of the application process may include images associated with each step of the application process, and/or videos associated with each step of the application process. The method 300 may further include displaying the AR preview of the selected makeup look, and/or the AR preview of the steps of the application process for the selected makeup look, via an integrated user interface of the handheld makeup applicator. In embodiments in which the user interface is part of a separate device, the method 300 may include sending the AR preview to the separate device to be displayed by the user interface of the separate device, e.g., via a network (e.g., network 108), via a short range signal between the separate device and the handheld makeup applicator device, and/or via a wired connection between the separate device and the handheld makeup applicator device.

Additionally, the method 300 may include controlling (block 306) one or more haptic feedback components to provide haptic feedback as the user holds the handheld makeup applicator device to the face of the user, based on a location of the handheld makeup applicator device with respect to the one or more facial features of the face of the user.

For instance, the method 300 may include providing haptic feedback in real-time to guide a user to move the handheld makeup applicator closer to facial features or areas of interest, to guide the user to bring the handheld makeup applicator to the appropriate facial area (e.g., lips for a lipstick applicator, eyelids for an eyeshadow applicator, cheeks for a blush applicator, etc.). Furthermore, the method 300 may include providing haptic feedback in real-time to guide a user to apply a cosmetic product, indicating one or more improvements or corrections suggested for the user.

For instance, one type of haptic feedback (e.g., a particular pattern or intensity of haptic feedback) may be provided when the user brings the handheld makeup applicator device closer to a facial feature of interest, while another type of haptic feedback (and/or the presence of haptic feedback) may be provided when the user moves the handheld makeup applicator device further from a facial feature of interest. As another example, the intensity of the haptic feedback may gradually be increased as the user brings the handheld makeup applicator device closer and closer to a facial feature of interest. As still another example, the type or intensity of the haptic feedback may vary based on which facial feature the user approaches using the handheld makeup applicator device. For instance, one type of haptic feedback (e.g., a particular pattern or intensity of haptic feedback) may be provided when the user brings the handheld makeup applicator device closer to his or her right eye, while another type of haptic feedback may be provided when the user brings the handheld makeup applicator device closer to his or her left eye.

Additionally, in some examples, the haptic feedback may be provided based on the location or proximity of a particular portion of the handheld makeup applicator device with respect to a facial feature of interest. For instance, the haptic feedback may be provided specifically based on the brush head of an applicator for eyeshadow moving closer to the eyelid of the user, or specifically based on the spoolie brush of a mascara applicator moving closer to the eyelashes of the user, to provide a few examples.

Moreover, in some examples, for instance, the haptic feedback may be provided when the user has moved an applicator outside of a range associated with the makeup look selected by the user, such that the user may be alerted to move the applicator within the range associated with the selected makeup look. For instance, one type of haptic feedback (and/or the absence of haptic feedback) may be provided when the user uses the applicator to draws a straight line across a user's eyelid for a cat eye look, and another type of haptic feedback (and/or the presence of haptic feedback) may be provided when the user begins to draw a crooked line or otherwise veers from an initial straight line. As another example, a first type of haptic feedback may be provided when the user holds an applicator too close to the eye to apply mascara, a second type of haptic feedback (or the same type of haptic feedback as the first type of haptic feedback) may be provided when the user holds the applicator too far from the eye to apply mascara, and a third type of haptic feedback (or the absence of haptic feedback) may be provided when the user holds the applicator the correct distance from the eye to apply mascara. As still another example, one type of haptic feedback may be provided when the user presses an applicator too hard on the lips to apply lipstick in accordance with the selected look, and another type of haptic feedback (or the absence of haptic feedback) may be provided when the user presses the applicator to the lips with the correct level of pressure to apply lipstick in accordance with the selected look.

Furthermore, in some examples, the haptic feedback may be provided on a particular side or portion of the handheld makeup applicator device to indicate that the user should move the handheld makeup applicator device. For instance, haptic feedback provided on the left side of the handheld makeup applicator device may indicate that the user should move the handheld makeup applicator device to the left to apply the cosmetic product across the face of the user, while haptic feedback provided on the right side of the handheld makeup applicator device may indicate that the user should move the handheld makeup applicator device to the right to apply the cosmetic product across the face of the user.

Moreover, in some examples, the method 300 may further include analyzing the sensor data in real-time to identify blemishes of the skin of the user, and automatically adjusting the haptic feedback, based on identified blemishes, i.e., beyond the initial parameters of the selected makeup look. For instance, the method 300 may include adjusting the guidance to such that the user applies a different amount of particular cosmetic product, e.g., to add more foundation or concealer, to an area of the user's face including a blemish, in order to cover the blemish with the cosmetic product. Furthermore, in some examples, the method 300 may include analyzing the sensor data in real-time to determine whether the blemish is sufficiently covered based on an initial application of the cosmetic product, and may include automatically adjusting the guidance and/or haptic feedback such that the user adds additional cosmetic product as needed until the blemish is sufficiently covered.

Additionally, in some examples, the method 300 may further include analyzing the sensor data in real-time to identify skin reactions of the skin of the user, and automatically generating alerts or notifications based on any identified skin reactions. For instance, the method 300 may include presenting such generated alerts via an integrated user interface, and/or sending such generated alerts to a separate device to be displayed via a user interface of the separate device.

Furthermore, in some examples, the method 300 may include capturing data associated with packaging of various cosmetic products (i.e., cosmetic products to be added to integrated dispensers of the handheld applicator device, and/or cosmetic products stored separately from the handheld applicator device), and analyzing the data associated with the packaging of the various cosmetic products to identify respective cosmetic products based on their packaging. For instance, in some examples, this analysis may include capturing an image of a cosmetic product package and using object recognition techniques to identify a likely type of cosmetic product and/or likely properties associated with the cosmetic product based on the image. Moreover, in some examples, this analysis may include analyzing an image of the cosmetic product packaging using optical character recognition techniques to identify one or more letters, numbers, words, codes, etc., on the cosmetic product packaging, and accessing a database associated with cosmetic products to match any identified letters, numbers, words, codes, etc., on the cosmetic product packaging with particular cosmetic products and/or particular properties associated therewith. As another example, this analysis may include analyzing an image of the cosmetic product packaging to identify and/or decode a barcode, QR code, etc. For instance, the payload of the barcode, QR code, etc., may include an identification or indication of the cosmetic product and/or properties associated therewith. Moreover, in some examples, the method 300 may include identifying a cosmetic product and/or properties associated therewith based on input provided by a user (e.g., input provided via an integrated user interface of the handheld makeup applicator device, and/or via a user interface of a separate device that is sent to the handheld makeup applicator device). The method 300 may further include adjusting the haptic feedback based on particular cosmetic products being applied using the handheld makeup applicator device, and/or properties associated therewith.

In some examples, the method 300 may further include receiving feedback associated with the haptic feedback and/or the makeup look created using the haptic feedback from the user (e.g., via a user interface) subsequent to the application of one or more cosmetic products to the face of the user, and storing the feedback associated with the makeup look. For instance, the method 300 may update the haptic feedback in future applications based on feedback provided by the user.

Additional Considerations

The following additional considerations apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, nonvolatile memory, or a combination thereof), registers, or other machine components that receive, store, transmit, or display information.

As used herein any reference to "one embodiment" or "an embodiment" or "some embodiments" means that a particular element, feature, structure, or characteristic described in connection with the embodiment is included in at least one embodiment. The appearances of the phrase "in one embodiment" or "in some embodiments" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a handheld makeup applicator device, and/or systems, methods, and/or techniques associated therewith. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

Aspects

1. A handheld makeup applicator device, comprising: one or more sensors operable to capture real-time data associated with a face of a user; one or more haptic feedback components operable to vibrate to provide haptic feedback to the user; and a controller, comprising: one or more processors; and one or more non-transitory memories storing computer-readable instructions that, when executed by the one or more processors, cause the one or more processors to: analyze the real-time data associated with the face of the user in order to generate a three-dimensional map associated with the face of the user; identify one or more facial features of the face of the user on the three-dimensional map associated with the face of the user; and control the one or more haptic feedback components to provide haptic feedback as the user holds the handheld makeup applicator device to the face of the user, based on a location of the handheld makeup applicator device with respect to the one or more facial features of the face of the user.

2. The handheld makeup applicator device of aspect 1, wherein the one or more sensors include one or more of a camera or a depth sensor.

3. The handheld makeup applicator device of any one of aspects 1 or 2, wherein the computer-readable instructions, when executed by the one or more processors, further cause the one or more processors to: receive, from a user interface associated with the handheld makeup applicator device, an indication of a makeup look selected by the user; and wherein controlling the one or more haptic feedback components to provide haptic feedback as the user holds the handheld makeup applicator device to the face of the user is further based on the makeup look selected by the user.

4. The handheld makeup applicator device of any one of aspects 1-3, wherein controlling the one or more haptic feedback components to provide haptic feedback as the user holds the handheld makeup applicator device to the face of the user includes modifying an intensity of the haptic feedback based on a proximity of the handheld makeup applicator device to a particular facial feature, of the one or more facial features of the face of the user.

5. The handheld makeup applicator device of any one of aspects 1-4, wherein controlling the one or more haptic feedback components to provide haptic feedback as the user holds the handheld makeup applicator device to the face of the user includes modifying a pattern of the haptic feedback based on a proximity of the handheld makeup applicator device to a particular facial feature, of the one or more facial features of the face of the user.

6. The handheld makeup applicator device of any one of aspects 1-5, wherein the one or more haptic feedback components include a first haptic feedback component associated with a first facial feature, of the one or more facial features of the face of the user, and a second haptic feedback component associated with a second facial feature, of the one or more facial features of the face of the user.

7. The handheld makeup applicator device of aspect 6, wherein the haptic feedback provided by the first haptic feedback component has a first pattern and wherein the haptic feedback provided by the second haptic feedback component has a second pattern.

8. The handheld makeup applicator device of aspect 6, wherein the haptic feedback provided by the first haptic feedback component has a first intensity and wherein the haptic feedback provided by the second haptic feedback component has a second intensity.

9. The handheld makeup applicator device of aspect 6, wherein the first haptic feedback component is located on a first portion of the handheld makeup applicator device and wherein the second haptic feedback component is located on a second portion of the handheld makeup applicator device, separate from the first portion of the handheld makeup applicator device.

10. The handheld makeup applicator device of any one of aspects 1-9, wherein the computer-readable instructions, when executed by the one or more processors, further cause the one or more processors to identify one or more blemishes of the face of the user on the three-dimensional map associated with the face of the user, and wherein controlling the one or more haptic feedback components to provide haptic feedback as the user holds the handheld makeup applicator device to the face of the user is further based a location of the handheld makeup applicator device with respect to the identified one or more blemishes of the face of the user.

11. The handheld makeup applicator device of aspect 10, wherein controlling the one or more haptic feedback components to provide haptic feedback as the user holds the handheld makeup applicator device to the face of the user, based on a location of the handheld makeup applicator device with respect to the one or more facial features of the face of the user, includes controlling the one or more haptic feedback components to provide haptic feedback based on a location of a portion of the handheld makeup applicator device, associated with applying a particular cosmetic product, with respect to a particular facial feature of the face of the user to which the particular cosmetic product is to be applied.

12. The handheld makeup applicator device of any one of aspects 1-11, wherein the computer-readable instructions, when executed by the one or more processors, further cause the one or more processors to: analyze the real-time data associated with the face of a user to identify a skin reaction; generate an alert based on the identified skin reaction; and wherein controlling the one or more haptic feedback components to provide haptic feedback as the user holds the handheld makeup applicator device to the face of the user includes controlling the one or more haptic feedback components to provide haptic feedback based on the generated alert.

13. The handheld makeup applicator device of any one of aspects 1-12, wherein the computer-readable instructions, when executed by the one or more processors, further cause the one or more processors to analyze one or more of: the real-time data associated with the face of the user captured by the one or more sensors, or previously-captured data associated with the face of the user captured by the one or more sensors, in order to determine one or more of a skin type or skin health condition associated with the user.

14. The handheld makeup applicator device of aspect 13, wherein analyzing one or more of: the real-time data associated with the face of the user captured by the one or more sensors, or previously-captured data associated with the face of the user captured by the one or more sensors, in order to determine one or more of the skin type or the skin health condition associated with the user, includes applying a trained machine learning model to one or more of the real-time data associated with the face of the user captured by the one or more sensors, or previously-captured data associated with the face of the user captured by the one or more sensors, to determine one or more of the skin type or the skin health condition associated with the user.

15. The handheld makeup applicator device of aspect 14, wherein the computer-readable instructions, when executed by the one or more processors, further cause the one or more processors to: obtain training data including data associated with faces of individuals as captured by one or more sensors, and corresponding skin types and/or skin health conditions associated with the respective individuals; and train a machine learning model, using the training data, to identify one or more of a skin type or a skin health condition associated with a new individual based on data associated with the face of the new individual as captured by one or more sensors, resulting in the trained machine learning model.

16. The handheld makeup applicator device of any one of aspects 1-15, wherein identifying the one or more facial features of the face of the user on the three-dimensional map associated with the face of the user includes applying a trained machine learning model to the three-dimensional map associated with the face of the user to identify the one or more facial features of the face of the user.

17. The handheld makeup applicator device of aspect 16, wherein the computer-readable instructions, when executed by the one or more processors, further cause the one or more processors to: obtain training data including three-dimensional maps associated with faces of individuals and corresponding facial features of the faces of the respective individuals; and train a machine learning model, using the training data, to identify one or more facial features of a face of a new individual based on a three-dimensional map associated with the face of the new individual, resulting in the trained machine learning model.

18. The handheld makeup applicator device of any one of aspects 1-17, wherein the computer-readable instructions, when executed by the one or more processors, further cause the one or more processors to: generate real-time guidance to the user based on the real-time data associated with the face of the user as the user uses the handheld makeup applicator device, the real-time guidance including one or more adjustments associated with the application of one or more cosmetic products to the face of the user; and wherein controlling the one or more haptic feedback components to provide haptic feedback as the user holds the handheld makeup applicator device to the face of the user include controlling the one or more haptic feedback components to provide haptic feedback based on the generated guidance.

19. A computer-implemented method for controlling a handheld makeup applicator device via one or more processors, comprising: analyzing real-time data associated with a face of a user captured by one or more sensors in order to generate a three-dimensional map associated with the face of the user; identifying one or more facial features of the face of the user on the three-dimensional map associated with the face of the user; and controlling one or more haptic feedback components of the handheld makeup applicator device to automatically provide haptic feedback real-time as the user holds the handheld makeup applicator device to the face of the user, based on a location of the handheld makeup applicator device with respect to the one or more facial features of the face of the user.

20. A non-transitory computer-readable medium storing instructions for controlling a handheld makeup applicator device that, when executed by one or more processors, cause the one or more processors to perform a method comprising: analyzing real-time data associated with a face of a user captured by one or more sensors of the handheld makeup applicator device in order to generate a three-dimensional map associated with the face of the user; identifying one or more facial features of the face of the user on the three-dimensional map associated with the face of the user; and controlling one or more haptic feedback components of the handheld makeup applicator device to automatically provide haptic feedback in real-time as the user holds the handheld makeup applicator device to the face of the user, based on a location of the handheld makeup applicator device with respect to the one or more facial features of the face of the user.

What is claimed is:

1. A handheld makeup applicator device, comprising:
one or more sensors operable to capture real-time data associated with a face of a user;
one or more haptic feedback components including:
a first haptic feedback component associated with a first facial feature of the user, the first haptic feedback component operable to vibrate to provide, to the user, first haptic feedback corresponding to the first facial feature; and
a second haptic feedback component associated with a second facial feature of the user, the second haptic feedback component operable to vibrate to provide, to the user, second haptic feedback corresponding to the second facial feature, wherein respective patterns and respective intensities of the first haptic feedback and of the second haptic feedback are modifiable, and the first facial feature and the second facial feature are different facial features of a set of facial features including a lip, a mouth, an eye, an eyelid, an eyebrow, a set of eyelashes, a lash line, a cheek, and a cheekbone; and
a controller, comprising:
one or more processors; and
one or more non-transitory memories storing computer-readable instructions that, when executed by the one or more processors, cause the one or more processors to:
analyze the real-time data associated with the face of the user in order to generate a three-dimensional map associated with the face of the user;
identify one or more facial features of the face of the user on the three-dimensional map associated with the face of the user;
control the haptic feedback component to modify one or more of the respective patterns of the first haptic feedback or the respective intensities of the first haptic feedback as the user holds the handheld makeup applicator device to the first facial feature of the user, based on the handheld makeup applicator device moving closer to the first facial feature; and
control the second haptic feedback component to modify one or more of the respective patterns of the second haptic feedback or the respective intensities of the second haptic feedback as the user holds the handheld makeup applicator device to the second facial feature of the user, based on the handheld makeup applicator device moving closer to the second facial feature.

2. The handheld makeup applicator device of claim 1, wherein the one or more sensors include one or more of a camera or a depth sensor.

3. The handheld makeup applicator device of claim 1, wherein:

the computer-readable instructions, when executed by the one or more processors, further cause the one or more processors to receive, from a user interface associated with the handheld makeup applicator device, an indication of a makeup look selected by the user; and the respective control of the first and the second haptic feedback components is further based on the makeup look selected by the user.

4. The handheld makeup applicator device of claim 1, wherein:

the respective intensities of the first haptic feedback is modified based on a proximity of the handheld makeup applicator device to the first facial feature; and the respective intensities of the second haptic feedback is modified based on a proximity of the handheld makeup applicator device to the second facial feature.

5. The handheld makeup applicator device of claim 1, wherein:

the respective pattern of the first haptic feedback is modified based on a proximity of the handheld makeup applicator device to the first facial feature; and the respective pattern of the second haptic feedback is modified based on a proximity of the handheld makeup applicator device to the second facial feature.

6. The handheld makeup applicator device of claim 1, wherein the first haptic feedback provided by the first haptic feedback component has a first pattern and wherein the second haptic feedback provided by the second haptic feedback component has a second pattern.

7. The handheld makeup applicator device of claim 1, wherein the first haptic feedback provided by the first haptic feedback component has a first intensity and wherein the second haptic feedback provided by the second haptic feedback component has a second intensity.

8. The handheld makeup applicator device of claim 1, wherein the first haptic feedback component is located on a first portion of the handheld makeup applicator device and wherein the second haptic feedback component is located on a second portion of the handheld makeup applicator device, the second portion being separate from the first portion of the handheld makeup applicator device.

9. The handheld makeup applicator device of claim 1, wherein:

the computer-readable instructions, when executed by the one or more processors, further cause the one or more processors to identify one or more blemishes of the face of the user on the three-dimensional map associated with the face of the user; and control of the one or more haptic feedback components is further based on a location of the handheld makeup applicator device with respect to the identified one or more blemishes of the face of the user.

10. The handheld makeup applicator device of claim 1, wherein control of the one or more haptic feedback components haptic feedback components is further based on a location of a portion of the handheld makeup applicator device, associated with applying a particular cosmetic product, with respect to a particular facial feature of the face of the user to which the particular cosmetic product is to be applied.

11. The handheld makeup applicator device of claim 1, wherein:

the computer-readable instructions, when executed by the one or more processors, further cause the one or more processors to analyze the real-time data associated with the face of a user to identify a skin reaction and generate an alert based on the identified skin reaction; and control of the one or more haptic feedback components is further based on the generated alert.

12. The handheld makeup applicator device of claim 1, wherein the computer-readable instructions, when executed by the one or more processors, further cause the one or more processors to analyze one or more of: the real-time data associated with the face of the user captured by the one or more sensors, or previously-captured data associated with the face of the user captured by the one or more sensors, in order to determine one or more of a skin type or skin health condition associated with the user.

13. The handheld makeup applicator device of claim 12, wherein the analysis of the one or more of: the real-time data associated with the face of the user captured by the one or more sensors or the previously-captured data associated with the face of the user captured by the one or more sensors includes an application of a trained machine learning model to the one or more of the real-time data associated with the face of the user captured by the one or more sensors or the previously-captured data associated with the face of the user captured by the one or more sensors to determine the one or more of the skin type or the skin health condition associated with the user.

14. The handheld makeup applicator device of claim 13, wherein the computer-readable instructions, when executed by the one or more processors, further cause the one or more processors to:

obtain training data including data associated with faces of individuals as captured by a plurality of sensors and corresponding skin types and/or skin health conditions associated with the individuals; and train a machine learning model, using the training data, to identify one or more of a skin type or a skin health condition associated with a new individual based on data associated with the face of the new individual as captured by the one or more sensors, thereby generating the trained machine learning model.

15. The handheld makeup applicator device of claim 1, wherein the identification of the one or more facial features of the face of the user on the three-dimensional map associated with the face of the user includes an application of a trained machine learning model to the three-dimensional map associated with the face of the user to identify the one or more facial features of the face of the user.

16. The handheld makeup applicator device of claim 15, wherein the computer-readable instructions, when executed by the one or more processors, further cause the one or more processors to:

obtain training data including three-dimensional maps associated with faces of individuals and corresponding facial features of the faces of the individuals; and train a machine learning model, using the training data, to identify one or more facial features of a face of a new individual based on a three-dimensional map associated with the face of the new individual, thereby generating the trained machine learning model.

17. The handheld makeup applicator device of claim 1, wherein the computer-readable instructions, when executed by the one or more processors, further cause the one or more processors to:

generate real-time guidance to the user based on the real-time data associated with the face of the user as the user uses the handheld makeup applicator device, the real-time guidance including one or more adjustments associated with application of one or more cosmetic products to the face of the user; and wherein the respective control of the first and the second haptic feedback components is further based on the generated guidance.

18. A computer-implemented method for controlling a handheld makeup applicator device via one or more processors, comprising:

analyzing real-time data associated with a face of a user captured by one or more sensors in order to generate a three-dimensional map associated with the face of the user;

identifying one or more facial features of the face of the user on the three-dimensional map associated with the face of the user;

controlling a first haptic feedback component of the handheld makeup applicator device to automatically modify one or more of a pattern or an intensity of first haptic feedback provided by the first haptic feedback component as the user holds the handheld makeup applicator device to a first facial feature of the user, based on the handheld makeup applicator device moving closer to the first facial feature; and controlling a second haptic feedback component of the handheld makeup applicator device to automatically modify one or more of a pattern or an intensity of second haptic feedback provided by the second haptic component as the user holds the handheld makeup applicator device to a second facial feature of the user, based on the handheld makeup applicator device moving closer to the second facial feature, the first facial feature and the second facial feature being different facial features of a set of facial features including a lip, a mouth, an eye, an eyelid, an eyebrow, a set of eyelashes, a lash line, a cheek, and a cheekbone.

19. A non-transitory computer-readable medium storing instructions for controlling a handheld makeup applicator device that, when executed by one or more processors, cause the one or more processors to perform a method comprising:

analyzing real-time data associated with a face of a user captured by one or more sensors of the handheld makeup applicator device in order to generate a three-dimensional map associated with the face of the user;

identifying one or more facial features of the face of the user on the three-dimensional map associated with the face of the user;

controlling a first haptic feedback component of the handheld makeup applicator device to automatically modify one or more of a pattern or an intensity of first haptic feedback provided by the first haptic feedback component as the user holds the handheld makeup applicator device to a first facial feature of the user, based on the handheld makeup applicator device moving closer to the first facial feature; and controlling a second haptic feedback component of the handheld makeup applicator device to automatically modify one or more of a pattern or an intensity of second haptic feedback provided by the second haptic component as the user holds the handheld makeup applicator device to a second facial feature of the user, based on the handheld makeup applicator device moving closer to the second facial feature, the first facial feature and the second facial feature being different facial features of a set of facial features including a lip, a mouth, an eye, an eyelid, an eyebrow, a set of eyelashes, a lash line, a cheek, and a cheekbone.

* * * * *